(12) United States Patent
Lee et al.

(10) Patent No.: US 8,574,852 B2
(45) Date of Patent: Nov. 5, 2013

(54) METHOD FOR EVALUATING CELL AGING BY EXPRESSION LEVEL OF COFILIN

(75) Inventors: Yi-Jang Lee, Taipei (TW); Cheng-Han Tsai, Taipei (TW)

(73) Assignee: National Yang Ming University, Taipei (TW)

( * ) Notice: Subject to any disclaimer, the term of this patent is extended or adjusted under 35 U.S.C. 154(b) by 116 days.

(21) Appl. No.: 13/175,505

(22) Filed: Jul. 1, 2011

(65) Prior Publication Data

US 2013/0004962 A1    Jan. 3, 2013

(51) Int. Cl.
*G01N 33/53* (2006.01)

(52) U.S. Cl.
USPC .................................... 435/7.1; 436/518

(58) Field of Classification Search
None
See application file for complete search history.

(56) References Cited

U.S. PATENT DOCUMENTS

| | | | | |
|---|---|---|---|---|
| 2002/0197602 A1* | 12/2002 | Burmer et al. | | 435/6 |
| 2007/0275918 A1* | 11/2007 | Kiyokawa et al. | | 514/44 |
| 2009/0029461 A1* | 1/2009 | Choo et al. | | 435/357 |

OTHER PUBLICATIONS

L. Hayflick et al., "The Serial Cultivation of Human Diploid Cell Strains[1]" *Experimental Cell Research* 25, May 15, 1961, pp. 585-621.
M. Serrano et al., "Oncogenic *ras* Provokes Premature Cell Senescence Associated with Accumulation of p53 and P16[INK4a]", *Cell*, vol. 88, Mar. 7, 1997, pp. 593-602.
Q. Chen et al., "Uncoupling the Senescent Phenotype from Telomere Shortening in Hydrogen Peroxide-Treated Fibroblasts", *Experimental Cell Research* 265, 2001, pp. 294-303.
C. Frippiat et al., "Subcytotoxic $H_2O_2$ Stress Triggers a Release of Transforming Growth Factor-β1, Which Induces Biomarkers of Cellular Senescence of Human Diploid Fibroblasts" *The Journal of Biological Chemistry*, vol. 276, No. 4, Jan. 26, 2001, pp. 2531-2537.
P. Anderson "Actin in Young and Senescent Fibroblasts" *Biochem. J.* (1978), pp. 169-172.
E. Wang et al., "Increased Organization of Cytoskeleton Accompanying the Aging of Human Fibroblasts in Vitro" *Experimental Cell Research* 154 (1984) pp. 191-202.
K. Nishio et al., "Senescence and cytoskeleton: overproduction of vimentin induces senescent-like morphology in human fibroblasts" *Histochem Cell Biol.*, Sep. 14, 2001, pp. 321-327.
J. Bamburg et al., "Putting a new twist on actin: ADF/cofilins modulate actin dynamics" *trends in Cell Biology* (vol. 9) Sep. 1999, pp. 364-370.
J. Bamburg et al., "Roles of ADF/cofilin in actin polymerization and beyond" *F1000 Biology Reports 2010* 2:62, Aug. 19, 2010, 7 pages.
C. Yap et al., "The Motility of Glioblastoma Tumour Cells is Modulated by Intracellular Cofilin Expression in a Concentration-Dependent Manner" *Cell Motility and the Cytoskeleton* 60: 153-165 (2005).
C. Tsai et al., "Regulated expression of cofilin and the consequent regulation of $p27^{kip1}$ are essential for $G_1$ phase progression" *Cell Cycle* vol. 8, Issue 15, 1-10, Aug. 1, 2009.
G. Stein et al., "Origins of $G_1$ arrest in senescent human fibroblasts" *BioEssays* vol. 17, No. 6, (1995) pp. 537-543.
F. Bringold et al., "Tumor suppressors and oncogenes in cellular senescence" *Experimental Gerontology* 35 (2000) pp. 317-329.
M. Collado et al. "Inhibition of the Phosphoinositide 3-Kinase Pathway Induces a Senescence-like Arrest Mediated by $p27^{Kip1}$" *The Journal of Biological Chemistry* vol. 275, No. 29, Issue of Jul. 21, 2000, pp. 21960-21968.
Z. Chen et al., "Crucial role of p53 dependent cellular senescence in suppression of Pten-deficient tumorigenesis" *Nature*, Aug. 4, 2005; 436(7051) pp. 725-730.
G. Carlo et al., "N-cofilin is associated with neuronal migration disorders and cell cycle control in the cerebral cortex" *Genesis Dev.* 2007 21: pp. 2347-2357.
I. Kwak et al., "Nuclear Accumulation of Globular Actin as a Cellular Senescence Marker" *Cancer Research* 64, Jan. 15, 2004, pp. 572-580.
C. Lee et al., "Proteomic profiling and identification of cofilin responding to oxidative stress in vascular smooth muscle" *Proteomics* 2006, 6, pp. 6455-6475.
Y. Yoo et al., "Tyrosine phosphorylation of cofilin at Y68 by v-Src leads to its degradation through ubiquitin-proteasome pathway" *Oncogene* 2010 29, pp. 263-272.
T. Kuilman et al., "The essence of senescence" *Genes. Dev.*, 2010 24: (2010) pp. 2463-2479.

\* cited by examiner

*Primary Examiner* — Jacob Cheu
(74) *Attorney, Agent, or Firm* — Muncy, Geissler, Olds & Lowe, PLLC

(57) ABSTRACT

The present invention discloses a concept that the expression level of cofilin may reflect the senescent condition of a cell or tissue. According to the findings in present invention, a method for determining the cellular senescent condition in a cell or tissue sample by evaluating the expression level of cofilin is provided. The detection of the expression level of cofilin is also used to screen an effective compound or composition for regulating the senescent condition in target cells.

20 Claims, 11 Drawing Sheets
(6 of 11 Drawing Sheet(s) Filed in Color)

WI-38

A

B

A

B

METHOD FOR EVALUATING CELL AGING BY EXPRESSION LEVEL OF COFILIN

BACKGROUND OF THE INVENTION

1. Brief Discussion of the Related Art

Since ancient times, people keep seeking for the way or panacea to preserve youth and immortality. In recent years, a fashion of anti-aging slowly spread to the global with the successive development and marketing of anti-aging products. In Japan, for instance, more than 70% people become aware of anti-aging. People in Taiwan also gradually increase the concern for anti-aging, which will promote the marketing of anti-aging products, and is expected to continue expanding in the global market.

Taking the case of anti-aging products marketing in Taiwan as an example, market scale of which has been grown by 17 times within the last decade, with increased from the sum of business of 20 billion NT dollars in 2001 to 25.7 billion NT dollars in 2002, and to 41.2 billion NT dollars in 2006. The estimated business in the next 10 years will be raised to 400 billion NT dollars. This shows that consuming power in the market of anti-aging beauty and health care products is really amazing, and is not influenced by the economic cycle. Therefore, it is in need of developing a high-throughput assay for rapid and efficient screening anti-aging agents in known artificial drugs or natural products.

When human cells are placed in a culture environment, they exhibit a finite proliferative capacity and are usually able to divide only forty to sixty times before reaching a senescent (nondividing) phase. The limited proliferative capacity of human cells in a culture environment is thought to result from multiple environmental and genetic mechanisms, and has been widely used as a model of human aging.

Cellular senescence was observed and proposed as a model for aging at the cellular level over thirty years ago. Leonard Hayflick studied human fibroblast like cells obtained from lung and skin. Hayflick found that when serially cultured, these cells would undergo rounds of divisions, but as the culture aged, the cells were no longer able to divide. In conjunction with the loss of division potential, there were changes in the morphology, the shape and physical appearance, of cells. The cells enlarged significantly, and more space was observed between individual cells.

In prior art, senescence-associated β-galactosidase (SA-β-gal) assay has been used in determination of cellular senescence in culture. The assay is based on finding that senescence induces the increase in levels of lysosomal β-galactosidase. In nonsenescent cells, the lysosomal hydrolase β-galactosidase cleaves galactose from glycoproteins at an optimum pH of 4.0 to 4.5. Lysosomal β-galactosidase activity can be detected in most mammalian cells by performing a cytochemical assay at pH 4.0 in which cleavage of X-gal by β-galactosidase leads to the formation of a blue precipitate. However, during senescence, there is an increase in lysosomal β-galactosidase protein levels and an overall increase in lysosomal size. The increase in β-galactosidase levels allows the detection of β-galactosidase activity at the suboptimal pH of 6.0 during senescence (Kurz et al., 2000, *J Cell Sci.* 113: 3613-3622).

Telomere and telomerase assay is an alternative method used in determining cell aging. At the end of a chromosome is a telomere, which keeps chromosome protected and prevent it from fusing into rings or binding with other DNA. When a cell divides and copies DNA, the telomeres get snipped to enable the copying process. Researchers can use the length of a cell's telomeres to determine the cell's age and how many more times is will replicate. In 1985, scientists discovered telomerase, a reverse transcriptase composed of two primary components, the protein catalytic subunit, TERT, and the template RNA subunit, TR. This enzyme extends telomeres, rebuilding them to their former lengths, by using its own RNA as a template for adding nucleotides to the ends of chromosomes. Detection of the expression of human catalytic subunit of telomerase (hTERT) provides an assay for analysis of telomerase activity on its native substrate, telomeres.

2. Field of the Invention

In present invention, an analytic method of cell aging is provided by detecting the expression level of cofilin in target cells. Cofilin is a ~19 kD protein that can bind to actin filaments and promote their dynamics for motility, development, polarity or cytokinesis (Bamburg et al., 1999, *Trends Cell Biol* 9: 364-70). Three isoforms of cofilin, including non-muscle cofilin (n-cofilin), muscle cofilin (m-cofilin) and ADF, are expressed in mammals. Loss of cofilin expression leads to G2/M phase arrest, the formation of multinucleate cells and irreversible cell death (Bellenchi et al., 2007, *Genes Dev* 21: 2347-57). However, there are no related references ever disclosed the correlations of endogenous cofilin expression level and the cellular aging situation in target cells.

SUMMARY OF THE INVENTION

This invention is based on the unexpected discovery that cell aging (cellular senescence) is in direct proportion to expression level of cofilin, which is a ubiquitously expressed actin binding protein and responsible for the formation of actin cytoskeleton. Accordingly, significant increase in the expression level of cofilin may reflect the senescent condition of cell or tissue.

In one aspect, the present invention provides a screening method of aging resistant agent, comprising: (a) cultivating target cell for 5 to 7 generations at which cell is maintained young; detecting the expression level of cofilin in the young cell as a reference value; (b) administrating a candidate aging resistant agent to the young cell and culturing subsequently for at least 13 generations at which cell is considered as senescent; (c) detecting the expression level of cofilin in treated cell; (d) comparing the expression level of cofilin detected in the treated cell to the reference value obtained in step (a); and (e) evaluating the efficacy of the candidate anti-aging drug in reducing or suppressing the expression level of cofilin to determine whether the candidate aging resistant agent can inhibit the senescent condition of treated cell.

In one embodiment of the invention, the expression level of cofilin in senescent cells is more than 3 times, preferably 3-10 times, and more preferably 3-5 times higher than in young cells.

In another embodiment of the invention, the expression level of cofilin is determined by Western blotting analysis. In a further embodiment of the invention, comparison of the expression level of cofilin in senescent cell and young cell is carried by histoimmunostaining method.

In yet another embodiment of the invention, the screening method further comprises a reconfirming step using β-galactosidase assay to check the senescent condition in the treated cell.

In another aspect, this invention features a method of modulating cell aging, comprising controlling the states of cellular senescent by regulating the expression level of cofilin.

In one embodiment of the invention, the gene of cofilin is over-expressed to induce or improve cellular senescence in young cells. In further embodiment of the invention, the target cell is transfected with cofilin gene over-expression vector to increase the expression level of cofilin.

In another embodiment of the invention, the expression of cofilin is reduced or inhibited to arrest or slow down cell aging in older cells. In further embodiment of the invention, the progression of cellular senescent states is mitigated by knockdown of cofilin expression with interfering RNA (siRNA).

As used herein, the term "cell aging" and "cellular senescence" can be interchangeable, and refers to the result of a progressive decline in the proliferative capacity and life span of cells. Each cell is programmed for a certain number of cell divisions and at the end of that time proliferation halts. The cell enters a quiescent state after which it experiences cell death via the process of apoptosis.

Other features or advantages of the present invention will be apparent from the following drawings and detailed description of several embodiments, and also from the appending claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Further, any mechanism proposed below does not in any way restrict the scope of the claimed invention.

In the following examples, independent experiments were conducted for assessment of the statistical difference between the control and experimental groups. Statistical differences were determined using the Student's t test. Significantly different results were defined as $p<0.05$.

Example 1

The Consistence of Higher Expression Level of Cofilin with the X-gal Staining and Morphological Changes in Old WI-38 Cells Cell Culture.

Human diploid fibroblast WI-38 cell line was purchased from ATCC and cultured in Minimum Essential Medium (MEM) supplemented with 10% fetal bovine serum (FBS), 2 mM L-glutamate, and 50 U/ml penicillin (Sigma-Aldrich, Inc., St. Louis, Mo.). The pH value of DMEM was adjusted to 7.4. The population doublings (PD) was determined by the ATCC formula: PDL=3.32×log (total viable cells at harvest/total cells at seed). Cells were maintained in a 37° C., humidified incubator (5% $CO_2$ and 95% air) and passaged when they reached 80% confluence.

Senescence-Associated β-Galactosidase Assay.

Non-passaged cells were treated with doxycycline and were cultured up to seven days in 12-well plates. Media were removed from plates, and cells were washed with 1×PBS twice. Then, cells were fixed for five minutes with freshly prepared fixing solution (2% formaldehyde and 0.2% glutaraldehyde in 1×PBS). After being fixed, cells were washed with 1×PBS twice and stained with freshly prepared staining solution (1 mg/ml X-gal, 40 mM citric acid/sodium phosphate solution, 5 mM potassium ferricyanide, 5 mM potassium ferrocyanide, 150 mM NaCl, 2 mM $MgCl_2$ in pH 6). Staining continued for 16 hours in a 37° C. incubator. After being stained, cells were washed and immersed with 1×PBS. The blueness developed in senescent cells were quantified with an optic-fiber-based spectroscopic system and observed with an inverse phase contrast microscope (CK-40 Olympus Co, Japan). Pictures were taken with a digital camera (Canon, PowerShot A620) added onto the microscope.

Figure 1A:
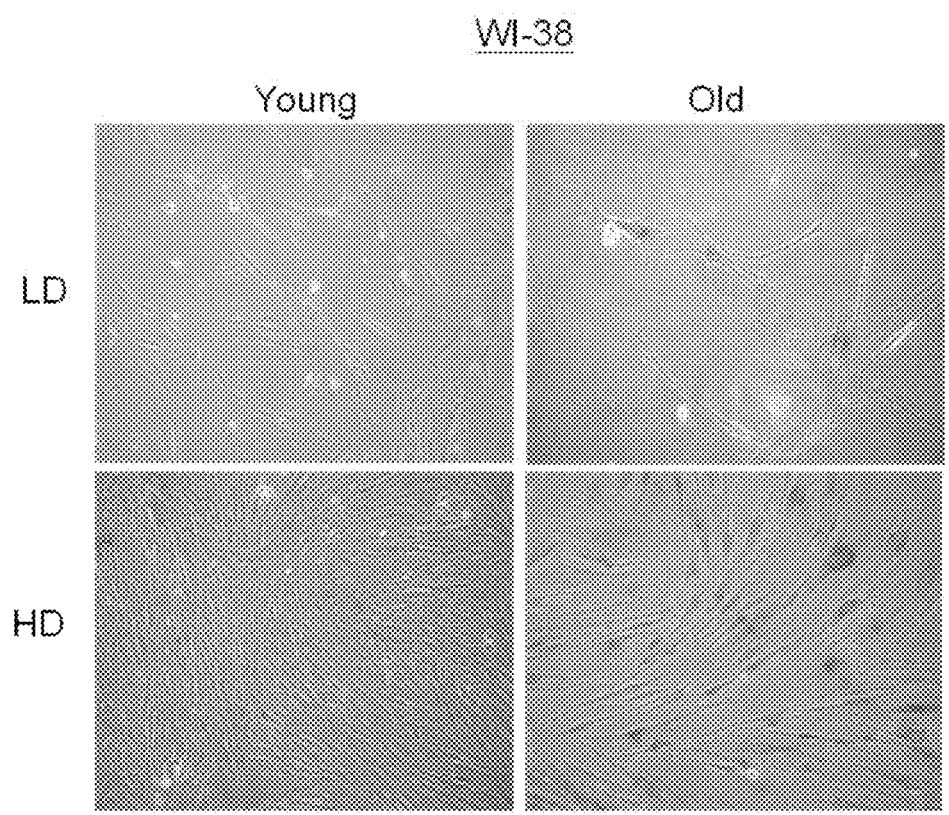
FIG. 1A shows comparative results of β-galactosidase staining and morphology viewed under light microscopy in young (cultured for 5 to 7 generations) and old (cultured for 13 to 15 generations) WI-38 cells. Senescent WI-38 cells exhibit strong perinuclear blue staining. Note the enlarged, flat morphology of the senescent WI-38 cells compared with the much smaller, spindle shaped morphology of the proliferating young WI-38 cells.

As showed in FIG. 1A, old WI-38 cells exhibit strong perinuclear blue staining, and an enlarged, flat morphology as compared with the much smaller, spindle shaped morphology of the young WI-38 cells.

Indirect Immunofluorescence Staining.

WI-38 cells ($1 \times 10^4$) were grown on 4-well chamber slides (Nalge Nunc International Corp., Naperville, Ill.) with or without doxycycline for 48 hr. Cells were then fixed with 4% paraformaldehyde in phosphate buffered saline (PBS) for 15 minutes at room temperature and permeabilized with 0.5% Triton X-100 for 5 minutes. For detection of $p27_{kip1}$ expression, fixed cells were incubated with the anti-cofilin (C-20) or anti-$p27_{kip1}$ antibody for 1 hr. After that, the slides were washed with PBS and incubated with rhodamine-conjugated secondary antibody for 45 minutes. Following the incubation with the secondary antibody, the slides were washed again and incubated with 10 ⌠g/ml of 4',6-diamidino-2-phenylindole (DAPI) to stain the nuclei. Finally, the slides were mounted with 90% glycerol containing 2% DABCO (Kodak, Rochester, N.Y.), sealed, and examined using a fluorescence microscope (Leica DM IRB, Wetzlar, Germany).

For fluorescent staining of the actin filaments (F-actin) and globular actin (G-actin), the A12397 fluorescien-conjugated phalloidin (Invitrogen Inc., Carlsbad, Calif.) and rhodamine-conjugated DNaseI (Invitrogen Inc., Carlsbad, Calif.) were used, respectively. Nuclear entry of the G-actin was also detected in old cells as compared to the young cells.

Figure 1B:
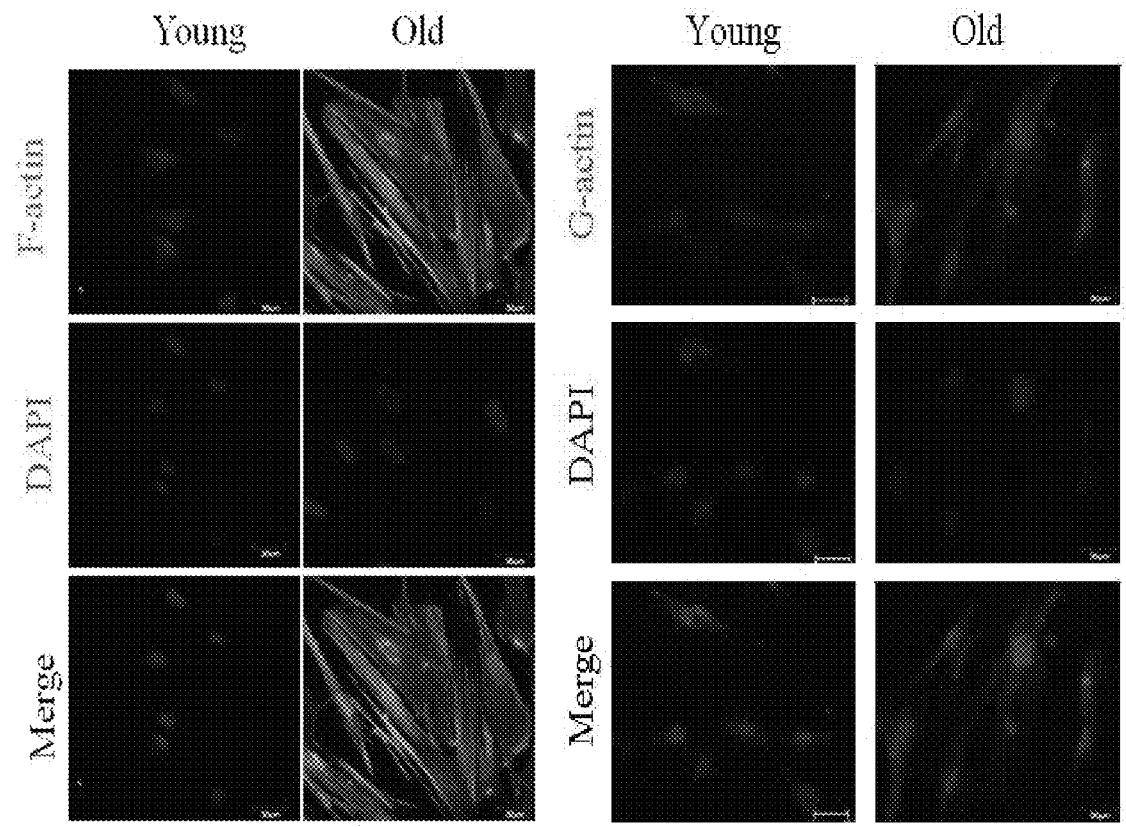
FIG. 1B shows the indirect immunofluorescence staining for cytoskeleton (F- and G-actin) in young and old WI-38 cells. Cell nuclei were visualized by DAPI staining. Three random fields under microscopy were detected for each experimental condition. For fluorescent staining of the actin filaments (F-actin) and globular actin (G-actin), the A12397 fluorescein-conjugated phalloidin and rhodamine-conjugated DNaseI were used, respectively. The results of A12397 fluorescein-conjugated phalloidin staining showed that cellular actin cytoskeletal mass was increased in the old cells as compared to the young cells. Nuclear entry of the G-actin was detected in old cells as compared to the young cells.

FIG. 1B shows the indirect immunofluorescence staining for cytoskeleton (F- and G-actin) in young and old WI-38 cells. Cell nuclei were visualized by DAPI staining. Three random fields under microscopy were detected for each experimental condition, and the results were consistent. The results of A12397 fluorescien-conjugated phalloidin staining showed that cellular actin cytoskeletal mass was increased in the old cells as compared to the young cells.

Western Blot Analysis.

Cell lysates were collected and subjected to SDS-polyacrylamide gel electrophoresis (SDS-PAGE) and western blot analysis as described previously ( ). Protein blotted membranes were probed with antibodies including anti-cofilin (C-20), anti-phospho-specific (ser3) cofilin (Millipore Inc., Billerica, Mass.), anti-$p27^{kip1}$, anti-$p21^{kip1}$ (BD Transduction Laboratories, San Diego, Calif.), anti-p53 (Santa Cruz Inc., Santa Cruz, Calif.), and anti-p16 antibodies (Santa Cruz Inc., Santa Cruz, Calif.). Immunoreactive protein bands were detected using the ECL chemiluminescence reagent (Amersham Bioscience, Buckinghamshire, UK) and visualized via exposure on X-ray film (Kodak, Rochester, N.Y.).

Figure 2A:
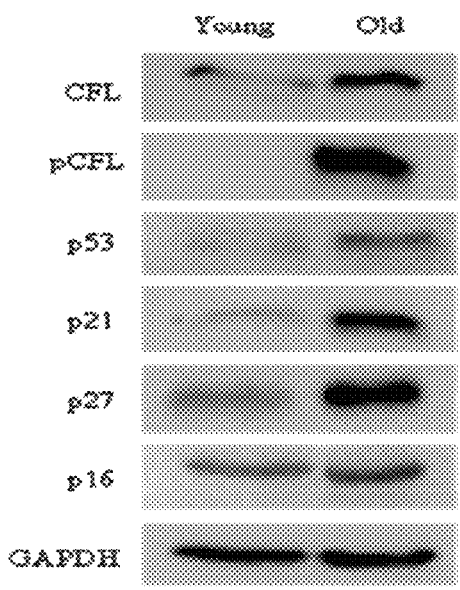
FIG. 2 is the diagram of Western blot analysis (A) and its quantitative result in OD value (B) showing expression level of protein cofilin, p-cofilin, p53, p21, p27, and p16 in young (cultured for 5 to 7 generations) and old (cultured for 13 to 15 generations) WI-38 cell.
Figure 2B:
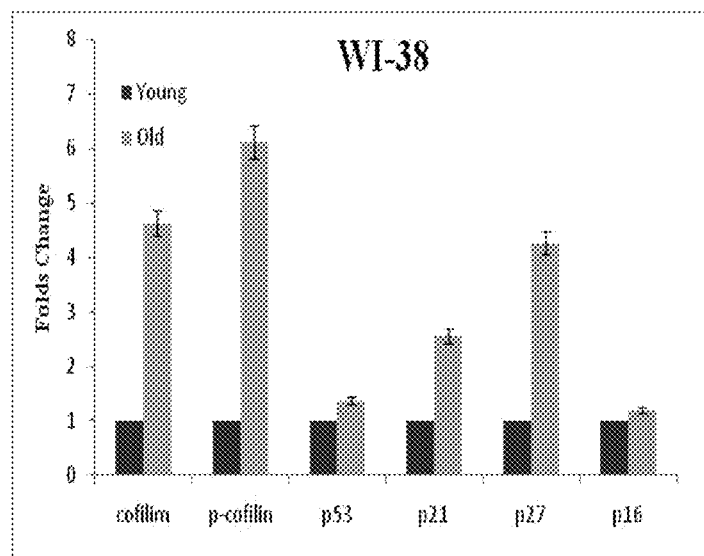

In FIG. 2, it is clear to see that cofilin and other known senescence-associated proteins, such as p53, p21, p27 and p16, were highly expressed in old WI-38 cells as compared to their expression levels in young cells.

Example 2

Higher Level of Cofilin Expression was Detected in the Tissues of Liver, Kidney, and Lung of Old Mouse than in Those of Young Mouse The relation of senescent conditions between the expression levels of cofilin was evaluated in the tissues of brain, liver, kidney, and lung sampled from old mouse (80 weeks old) and young mouse (6 week old). The brain, liver, kidney, and lung tissues sampled from old mouse 80 weeks old) and young mouse were Paraffin embedded for observing the expression level of cofilin in Immunohistochemistry assay. And for X-gal staining, the consecutive tissue slides were cryosection embedded, and subjected to the Senescence-associated β-galactosidase (SA-β-gal) assay as described in Example 1. In addition, the known senescence-associated marker p53 was detected to tissues from the aged mice for further correlating to the cofilin expression and the phenotypes of increased SA-β-gal biomarkers. For detailed immunohistochemistry assay, different tissues obtained from mice were rinsed with PBS and then fixed in 4% paraformaldehyde with gentle shaking at 4° C. overnight. The fixed sample was then embedded in OCT (optimal cutting temperature solution) and stored in −80° C. Five μm tissue sections were obtained from the OCT-embedded tissues. For immunohistochemical staining, the tissue sections were fixed in 4% paraformaldehyde 10 minutes at room temperature and subsequently blocked by using 5% peroxide ($H_2O_2$) and goat serum. Tissue sections were incubated with anti-ofilin (1:50, GeneTex Inc. Irvine, Calif.) or anti-p53 antibody (1:50, GeneTex Inc. Irvine, Calif.) antibodies at 37° C. for 1.5 hours. The slides then were incubated with horseradish peroxidase (HRP)-conjugated secondary antibody (1:400, Sigma-Aldrich, Inc., St. Louis, Mo.) at 37° C. for 1 hour. Finally, tissue sections were incubated with 3',3'-diaminobenzidine (DAKO Inc., Glostrup, Denmark) until a brown color was developed and further counterstained with hematoxylin and eosin (H&E). All pictures were captured using the optical microscopy (Olympus America Inc. Center Valley, Pa.).

Figure 3:
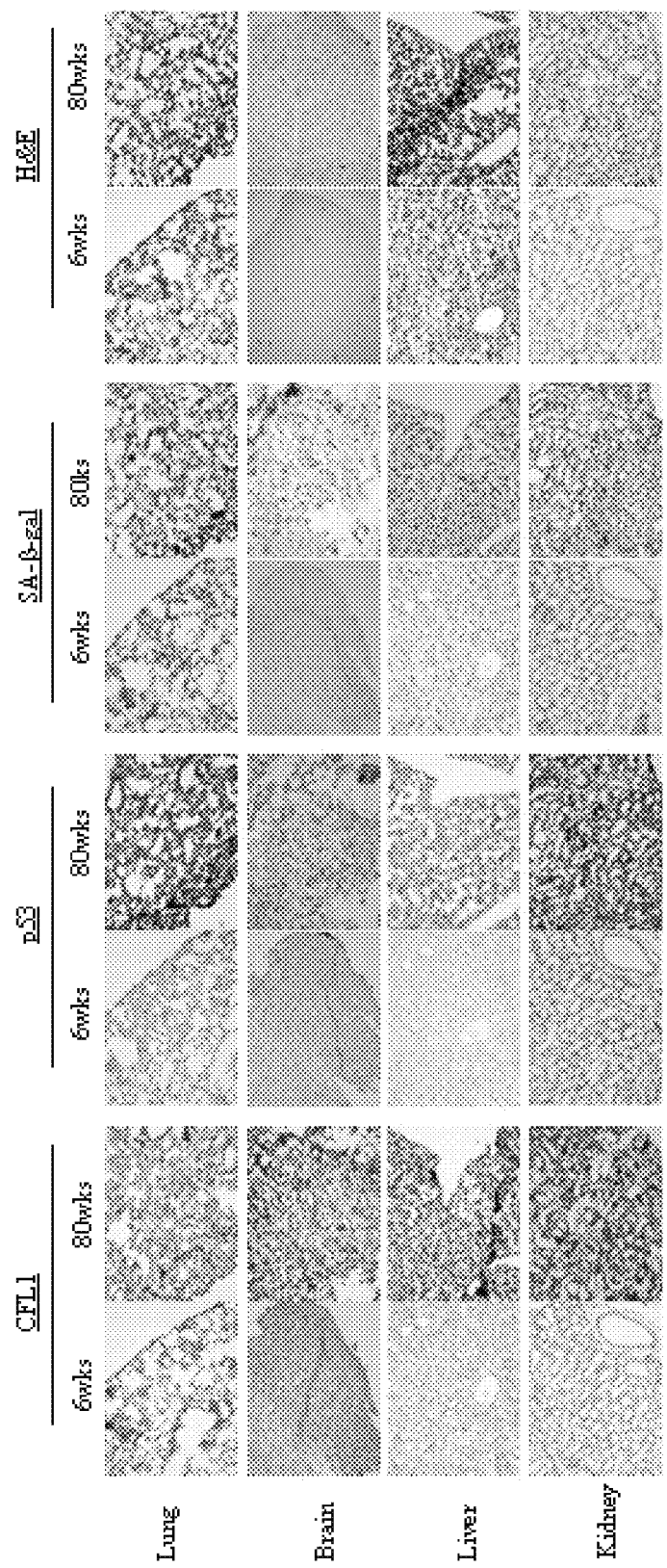
FIG. 3 shows the Immunohistochemistry of cofilin (left parallels) and the senescence-associated β-galactosidase staining (right parallels) viewed under light microscopy in the sections of lung, liver and kidney samples from young (6 weeks) and old (80 weeks) mice.

Results are showed in FIG. 3. In the about 1 y/o mouse, sections of the liver, kidney, and lung tissue samples displayed a significant X-gal staining signal. And correspondingly, the signal of cofilin Immunohistostaining in the liver, kidney, and lung tissues from the old mouse was higher than in young tissues. These results suggested that the increment of the expression level of cofilin is highly related to the aging process in living tissues.

Immunoprecipitation-Immunoblotting Assay.

In brief, tissues were cut and minced and the protein extraction was conducted by the TRIzol® reagent (Invitrogen). Equal amounts of protein extracts (500 μg) from different tissues were incubated with anti-cofilin1 antibody at 4° C. for 2 hr, and were subsequently mixed with Protein-A/G PLUS-agarose (Santa Cruz Inc., Santa Cruz, Calif.) overnight. Immunocomplexes were then washed with lysis buffer for four times and pellets were collected by centrifugation at 1,000×g. Washed immunocomplexes were mixed with 2× sample buffer and were ran on SDS-PAGE. Subsequently, gel was electrotransferred to PVDF membrane and again detected by anti-cofilin1 antibody. One tenth of the cell lysate without immunoprecipitation was immunoblotted using anti-GAPDH antibody as input controls.

Figure 4A:
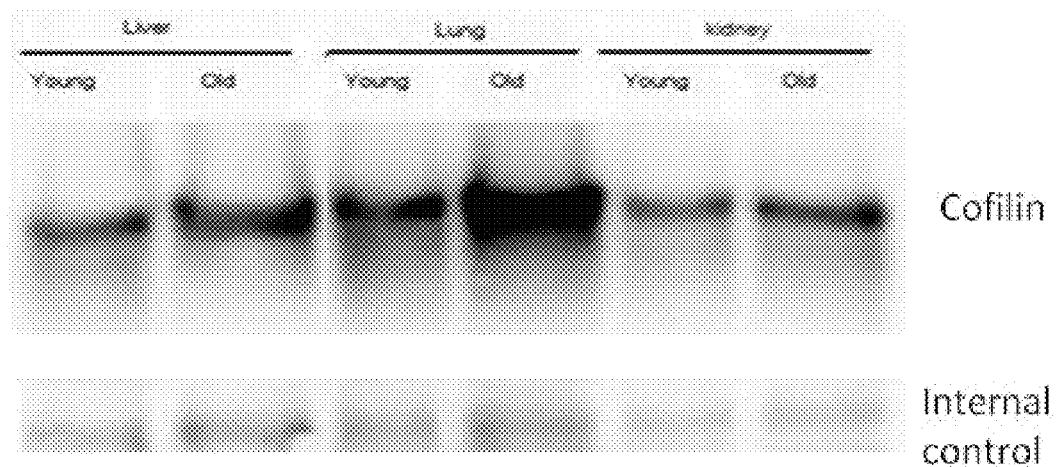
FIG. 4 is the diagram of Immunoprecipitation-immunoblotting assay (A) and its quantitative result in OD value (B) of extracted proteins showing the expression levels of cofilin in lung, liver and kidney tissues from young (6 weeks) and old (80 weeks) mice.
Figure 4B:
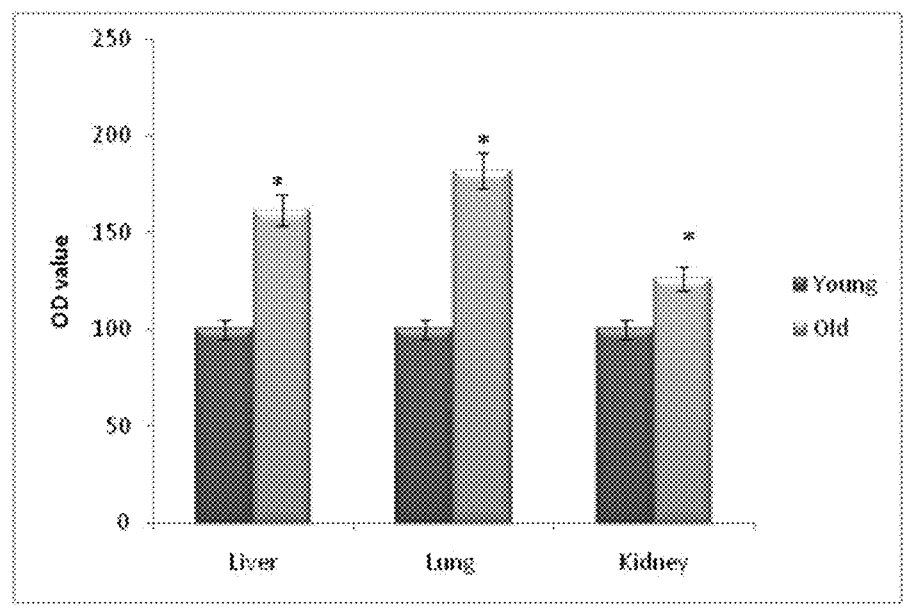

By the results showed in FIG. 4, the liver, kidney, and lung tissues from the old mouse exhibit higher expression level of cofilin than in young tissues.

Example 3

Establishment of Screening Plate for Anti-Aging Agents by Determining the Levels of Cofilin In this experiment, we used SK-II Pitera™, a well known anti-aging agent used in cosmetic formulations, to evaluate the performance for screening anti-aging agents. Human fibroblast WI-38 cells were cultured for 13 to 15 generations to reach a senescent situation. The culture conditions have been described above.

The old human fibroblast cells ($1\times10^4$) grown on 4-well chamber slides (Nalge Nunc International Corp., Naperville, Ill.) were treated with different percentage (0, 5, 10, and 20%, v/v) of Pitera™ for 48 hours, then subjected to senescence-associated β-galactosidase assay and Western blot analysis as described in Example 1.

Figure 5A:
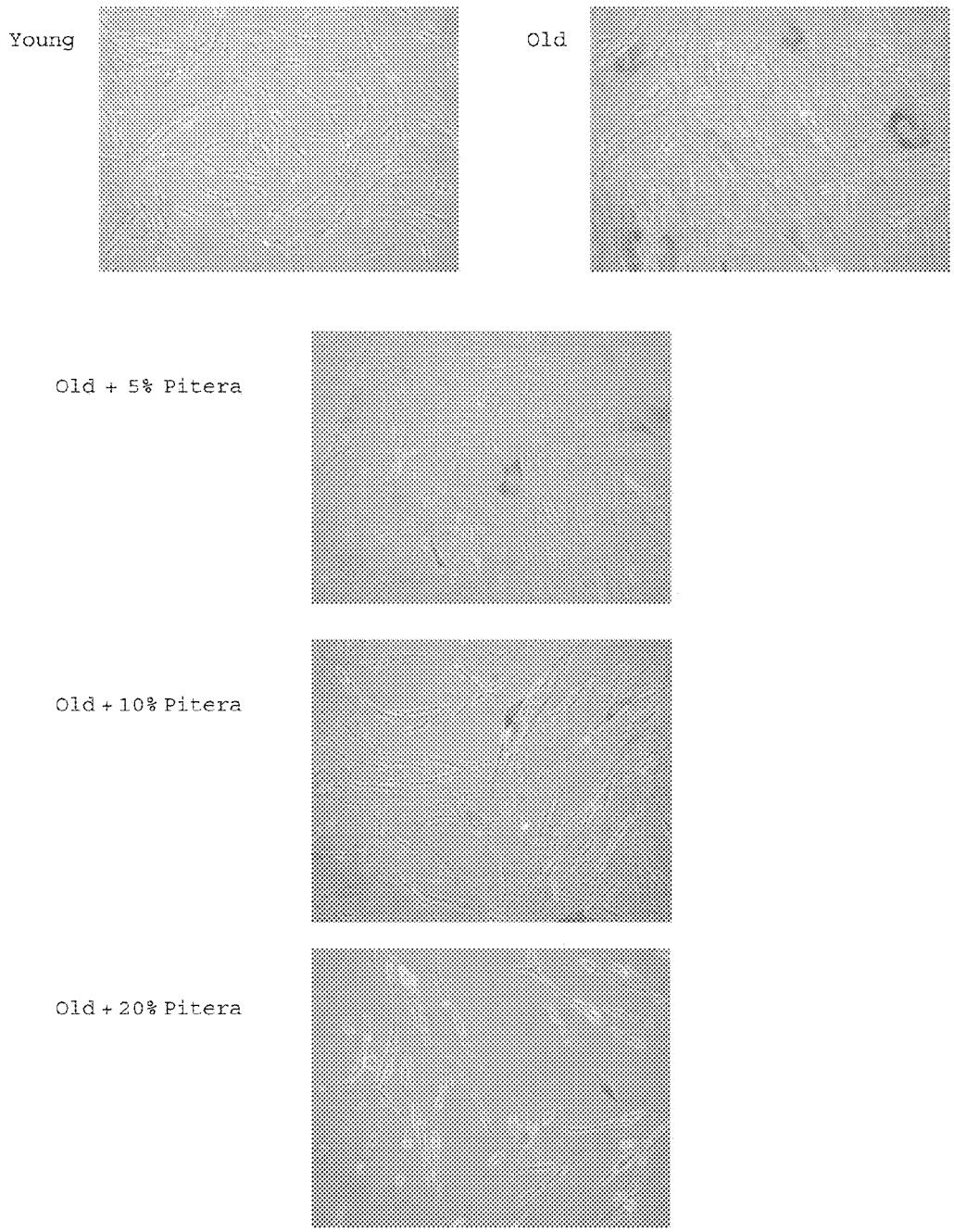
FIG. 5 is diagrams showing the reduction of senescence-associated β-galactosidase (SA-β-gal) biomarkers in old human fibroblasts by the SK-II Pitera™. (A) The random selected photos of young and old fibroblasts stained for SA-β-gal biomarkers. (B) quantification of the SA-β-gal stained cells under various conditions. Y axis is the percentage of cells with SA-β-gal biomarkers. One hundred cells were randomly counted, and three independent experiments were conducted. Each value represents the mean±S.D. *: $p<0.05$ compared to untreated old (O) fibroblasts.
Figure 5B:
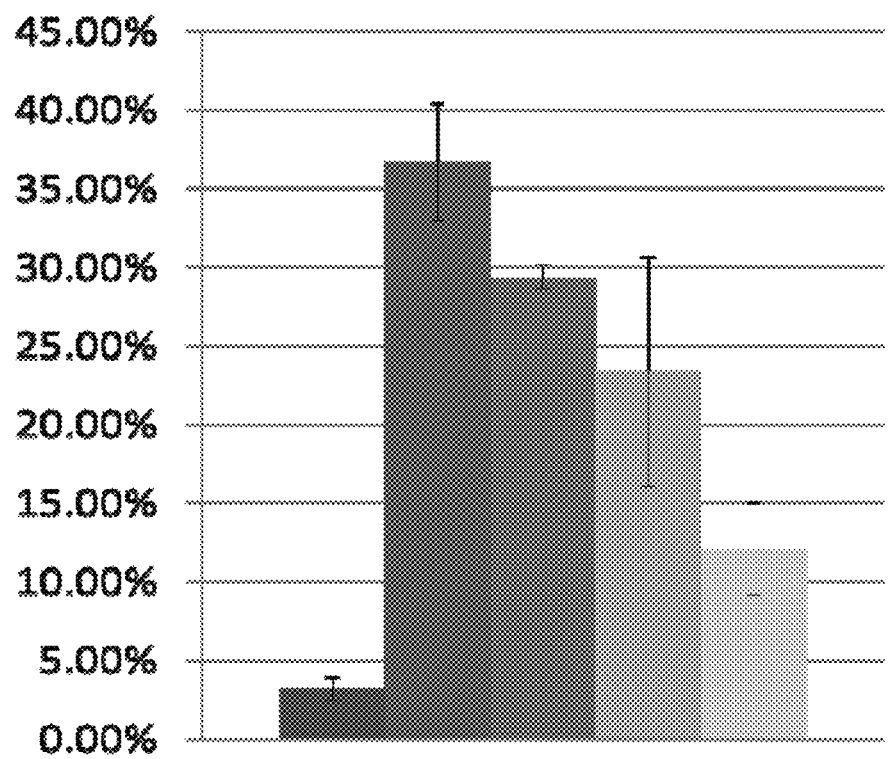

As showed in FIG. 5, old human fibroblast cells exhibit strong perinuclear blue staining. After the treatment of anti-aging agent SK-II Pitera™, the strength of the blue staining was reduced dose-dependently (FIG. 5A). FIG. 5B shows the quantification of the SA-β-gal stained cells under the various treating conditions.

Figure 6:
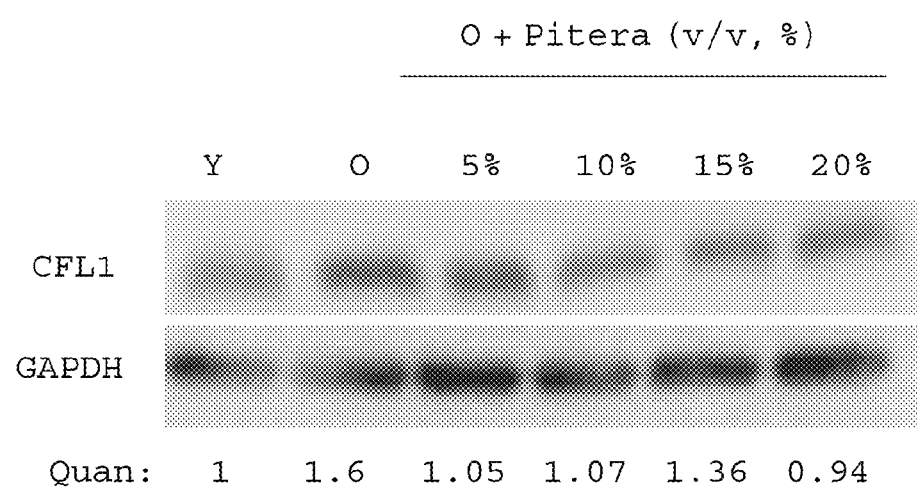
FIG. 6 shows the reductive effects of SK-II Pitera™ treatment on the senescence associated up-regulation of cofilin-1 in human diploid fibroblasts determined by Western blot analysis. The quantification results were obtained using densitometry (CFL1 was normalized by GADPH). GAPDH: internal control. Y: Young cells, O: old cells.

In FIG. 6, the Western blot analysis showed the levels of total cofilin-1 proteins under different experimental conditions. By the results, it is showed that senescence associated up-regulation of cofilin-1 in human diploid fibroblasts was down-regulated by SK-II Pitera™ a dose-dependent manner. Therefore, the efficiency of a compound or composition on anti-aging can be detected by determining the expression level of cofilin in cells or tissues after treatment of the compound or composition. The expression level of cofilin changed in the treated cells or tissues can be used as a screening plate for anti-aging agents.

Example 4

Modulating the States of Cellular Senescent by Regulating the Expression Level of Cofilin Induction of Cell Aging in Young WI-38 cell (7 passed WI-38) by Increasing the Expression Level of Cofilin Conlin (CFL) Gene Over Expression by pAS2 Vector.

$2.5\times10^6$ of human embryonic kidney 293T cells were co-transfected with the lentiviral plasmid pAS2-cofilin, and viral packaging plasmids including CMV-ΔR8.91 and pMDG after cells reached a confluency of 70%. The pAS2-cofilin plasmid contains a human cofilin coding sequence driven by a cytomegaloviral promoter. Additionally, the pAS3-EGFP plasmid that expresses green fluorescent protein but not cofilin was used as a negative control. After 16 hours of transfection, the supernatant was removed and was replaced by fresh medium containing 1% bovine serum albumin (BSA). The medium containing virus particles were collected twice at 24 hours and 36 hours of incubation. The collected virus soup was subjected to the ultracentrifugation at 110,000×g for 2 hours. The pellets were then dissolved in serum-free medium. For the infection of target cells, the virus soup was mixed with 8 µg/ml of polybrene (Sigma-Aldrich, Inc., St. Louis, Mo.) and added to the target cells for 24 hours. The virus containing medium was then replaced with the fresh medium for additional 24-48 hours before analysis.

Figure 7:
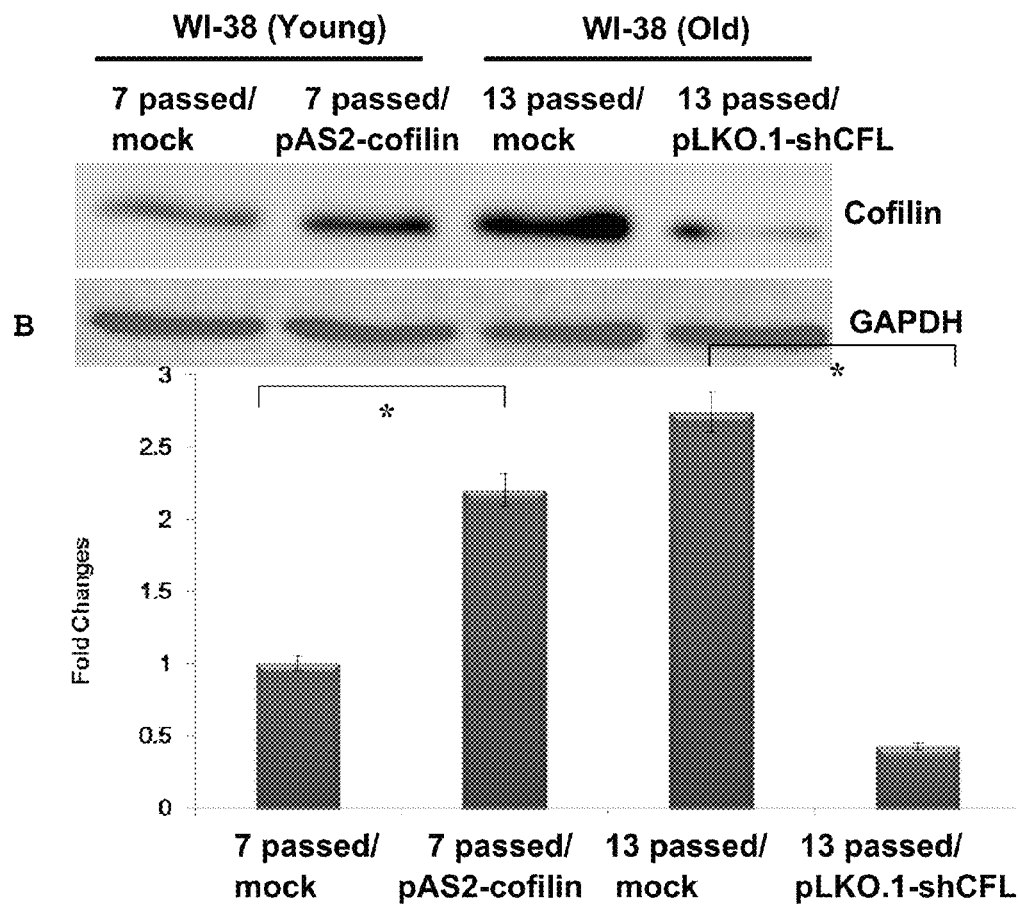
FIG. 7 is the diagram of Western blot analysis (A) and its quantitative result in OD value (B) showing the cofilin expression level in cofilin over expressed (by pAS2 vector) young WI-38 cells and cofilin gene knockdown (by siRNA) old WI-38 cells.
Figure 8:
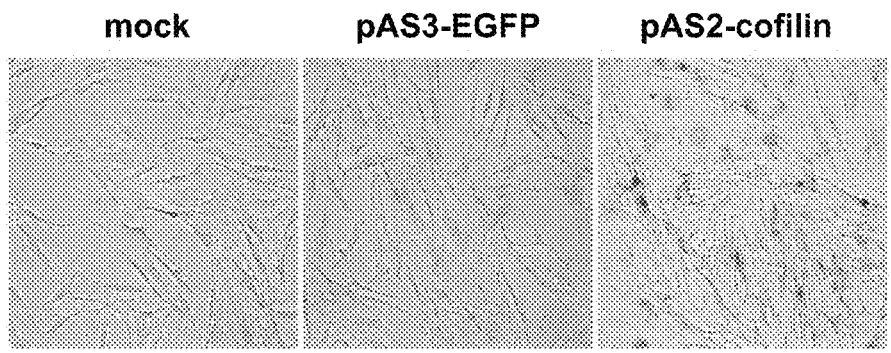
FIG. 8 shows the results of X-gal staining (A) and its quantitative result in OD value (B) in non-treated and cofilin over expressed young WI-38 cells. Cells transfected with pAS3-EGFP were used as negative control.
Figure 8:
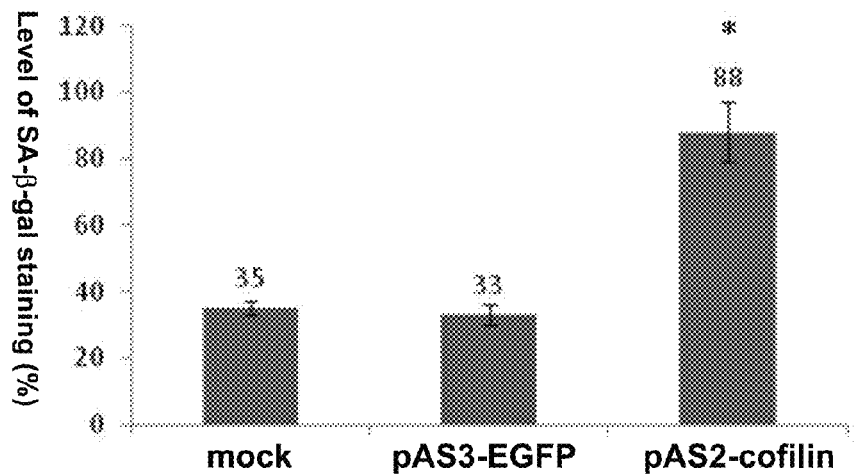

As showed in FIG. 7, cofilin protein was over-expressed in young (7 passed) WI-38 cells by lentiviral-mediated transduction of pAS2-cofilin plasmid as detected in Western blotting assay. In comparison with the results of senescence associated β-galactosidase (SA-β-gal) staining (showed in FIG. 8), the over-expressed cofilin gene can induce or promote cellular senescence in young WI-38 cells.

Alleviation of Cell Senescence in Old WI-38 Cell (13 Passed WI-38) by Decreasing the Expression Level of Cofilin.

Cofilin (CFL) Gene Knockdown by shRNA Targeting on Cofilin Gene.

$2.5\times10^6$ of human embryonic kidney 293T cells were co-transfected with the lentiviral plasmid pLKO.1-shCFL, (clone ID: TRCN0000029713) and viral packaging plasmids including CMV-ΔR8.91 and pMDG after cells reached a confluency of 70%. The sequence of shCFL can target to the cofilin mRNA and suppress the cofilin1 expression up to 98%. Expression of shCFL is driven by a U6 promoter on the pLKO.1 vector. After 16 hours of transfection, the supernatant was removed and was replaced by fresh medium containing 1% bovine serum albumin (BSA). The medium containing virus particles were collected twice at 24 hours and 36 hours of incubation. The collected virus soup was subjected to the ultracentrifugation at 110,000×g for 2 hours. The pellets were then dissolved in serum-free medium. For the infection of target cells, the virus soup was mixed with 8 µg/ml of polybrene (Sigma-Aldrich, Inc., St. Louis, Mo.) and added to the target cells for 24 hours. The virus containing medium was then replaced with the fresh medium for additional 24-48 hours before analysis.

Figure 9:
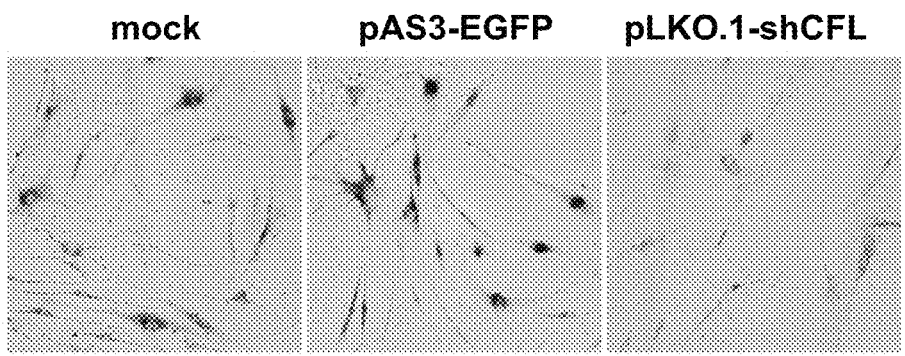
FIG. 9 shows the results of X-gal staining (A) and its quantitative result in OD value (B) in non-treated and cofilin gene knockdown old WI-38 cells. Cells transfected with pAS3-EGFP were used as negative control.
Figure 9:
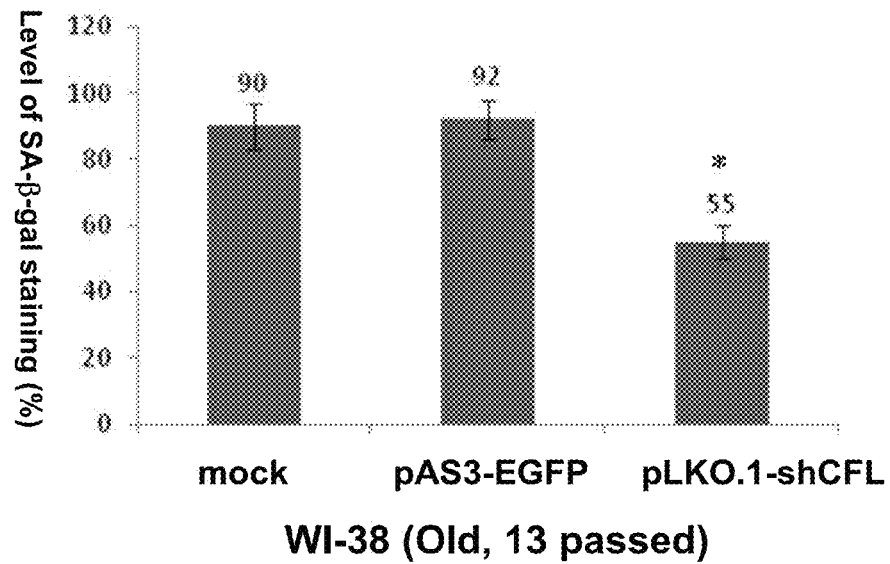

As shown in FIG. 9, decrease in expression level of cofilin can arrest or significantly slow down senescence progression in old WI-38 cell (WI-38 Y13).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for determining the cellular senescent condition in a cell or tissue sample, comprising:
   (a) detecting the expression level of cofilin in the cultured cell or tissue sampled from a target mammal;
   (b) comparing the expression level of cofilin detected in the cultured cell or tissue sample to the reference value obtained in the young cells cultivated for 5 to 7 generations; and
   (c) determining the senescent condition of the tested cell or tissue as evaluating whether the expression level of cofilin detected in step (a) is higher than in the young cells, and the tested cell or tissue is determined as being in senescent condition when the expression level of cofilin is more than 3 times higher than in the young cells.

2. The method of claim 1, wherein the expression level of cofilin is evaluated by Western blotting analysis.

3. The method of claim 1, wherein the expression level of cofilin is evaluated by histoimmunostaining assay.

4. The method of claim 1, wherein the tested cell or tissue is determined as being in senescent condition when the expression level of cofilin is 3-10 times higher than in the young cells.

5. The method of claim 1, wherein the tested cell or tissue is determined as being in senescent condition when the expression level of cofilin is 3-5 times higher than in the young cells.

6. The method of claim 1, which further comprises a reconfirming step using β-galactosidase assay to check the senescent condition in the treated cell.

7. A screening method of cell aging resistant agent, comprising: (a) cultivating target cell for 5 to 7 generations at which cell is maintained young, and detecting the expression level of cofilin in the young cell as a reference value;
　(b) administrating a candidate aging resistant agent to the young cell and culturing subsequently for at least 13 generations at which cell is considered as senescent;
　(c) detecting the expression level of cofilin in treated cell;
　(d) comparing the expression level of cofilin detected in the treated cell to the reference value obtained in step (a); and
　(e) evaluating the efficacy of the candidate anti-aging agent in reducing or suppressing the expression level of cofilin to determine whether the candidate aging resistant agent can inhibit the senescent condition of treated cell.

8. The screening method of claim 7, wherein the expression level of cofilin detected in the treated cells is more than 3 times higher than in young cells as being in senescent condition.

9. The screening method of claim 7, wherein the expression level of cofilin detected in the treated cells is 3-10 times higher than in young cells as being in senescent condition.

10. The screening method of claim 7, wherein the expression level of cofilin detected in the treated cells is 3-5 times higher than in young cells as being in senescent condition.

11. The screening method of claim 7, wherein the expression level of cofilin is determined by Western blotting analysis.

12. The screening method of claim 7, wherein the comparison of the expression level of cofilin in senescent cell and young cell is carried by histoimmunostaining method.

13. The screening method of claim 7, which further comprises a reconfirming step using β-galactosidase assay to check the senescent condition in the treated cell.

14. A screening method of cell aging inducer, comprising:
　(a) cultivating target cell for 5 to 7 generations at which cell is maintained young, and detecting the expression level of cofilin in the young cell as a reference value;
　(b) administrating a candidate aging inducer to the young cell;
　(c) detecting the expression level of cofilin in the treated cell
　(d) evaluating the efficacy of the candidate aging inducer in promoting the higher expression level of cofilin as compared with the reference value; and
　(e) determining whether the candidate agent can induce the senescent condition in the treated cell.

15. The screening method of claim 14, wherein the expression level of cofilin detected in the treated cells is more than 3 times higher than in young cells as being induced to senescent condition.

16. The screening method of claim 14, wherein the expression level of cofilin detected in the treated cells is 3-10 times higher than in young cells as being induced to senescent condition.

17. The screening method of claim 14, wherein the expression level of cofilin detected in the treated cells is 3-5 times higher than in young cells as being induced to senescent condition.

18. The screening method of claim 14, wherein the expression level of cofilin is determined by Western blotting analysis.

19. The screening method of claim 14, wherein the comparison of the expression level of cofilin in senescent cell and young cell is carried by histoimmunostaining method.

20. The screening method of claim 14, which further comprises a reconfirming step using β-galactosidase assay to check the senescent condition in the treated cell.

* * * * *